US00RE39089E

(19) United States
(12) Reissued Patent
Ralph et al.

(10) Patent Number: US RE39,089 E
(45) Date of Reissued Patent: May 2, 2006

(54) POLYAXIAL PEDICLE SCREW HAVING A THREADED AND TAPERED COMPRESSION LOCKING MECHANISM

(75) Inventors: James D. Ralph, Seaside Park, NJ (US); Stephen Tatar, Montvale, NJ (US); Joseph P. Errico, Green Brook, NJ (US); Thomas J. Errico, Summit, NJ (US)

(73) Assignee: Fastenetix, LLC, Summit, NJ (US)

(21) Appl. No.: 09/992,612

(22) Filed: Nov. 13, 2001

Related U.S. Patent Documents

Reissue of:
(64) Patent No.: 5,882,350
Issued: Mar. 16, 1999
Appl. No.: 09/002,535
Filed: Jan. 2, 1998

U.S. Applications:
(63) Continuation of application No. 09/774,915, filed on Jan. 30, 2001, now Pat. No. Re. 37,665, which is a continuation-in-part of application No. 08/843,972, filed on Apr. 17, 1997, now Pat. No. 5,888,204, which is a continuation-in-part of application No. 08/632,560, filed on Apr. 15, 1996, now Pat. No. 5,725,588, which is a continuation-in-part of application No. 08/421,087, filed on Apr. 13, 1995, now Pat. No. 5,520,690, and a continuation of application No. 08/835,909, filed on Apr. 10, 1997, now abandoned, which is a continuation-in-part of application No. 08/663,383, filed on Jun. 13, 1996, now Pat. No. 5,669,911, which is a continuation-in-part of application No. 08/559,196, filed on Nov. 13, 1995, now abandoned, which is a continuation-in-part of application No. 08/421,087, filed on Apr. 13, 1995, now Pat. No. 5,520,690.

(51) Int. Cl.
*A61B 17/70* (2006.01)

(52) U.S. Cl. ..... 606/61; 606/73
(58) Field of Classification Search ..... 606/60, 606/61, 69, 70, 71, 72, 73
See application file for complete search history.

(56) References Cited

U.S. PATENT DOCUMENTS 5,207,678 A * 5/1993 Harms et al. ..... 606/61
5,443,467 A * 8/1995 Biedermann et al. ..... 606/65
5,520,690 A * 5/1996 Errico et al. ..... 606/61
5,531,746 A * 7/1996 Errico et al. ..... 606/61
5,607,426 A * 3/1997 Ralph et al. ..... 606/61
5,669,911 A * 9/1997 Errico et al. ..... 606/61
5,672,176 A * 9/1997 Biedermann et al. ..... 606/61

* cited by examiner

*Primary Examiner*—David O. Reip
(74) *Attorney, Agent, or Firm*—Carter, DeLuca, Farrell & Schmidt, LLP

(57) ABSTRACT

A polyaxial orthopedic device for use with rod implant apparatus includes a screw having a curvate head, a two-piece interlocking coupling element which mounts about the curvate head, and a rod receiving cylindrical body member having a tapered socket into which both the screw and the interlocking coupling element are securely nested. The interlocking coupling element includes a socket portion which is slotted and tapered so that when it is radially compressed by being driven downwardly into the tapered socket in the cylindrical body it crush locks to the screw. The securing of the rod in the body member provides the necessary downward force onto the socket portion through a contact force on the top of the cap portion. Prior to the rod being inserted, therefore, the screw head remains polyaxially free with respect to the coupling element and the body. In a preferred embodiment, the cap portion and the socket portion are formed and coupled in such a way that when the cap portion is compressed toward the socket portion, there is an additional inward radial force applied by the cap portion to the socket portion, thereby enhancing the total locking force onto the head of the screw.

20 Claims, 9 Drawing Sheets

POLYAXIAL PEDICLE SCREW HAVING A THREADED AND TAPERED COMPRESSION LOCKING MECHANISM

Matter enclosed in heavy brackets [ ] appears in the original patent but forms no part of this reissue specification; matter printed in italics indicates the additions made by reissue.

CROSS-REFERENCE TO PRIOR APPLICATION

This application is a *continuation of U.S. patent application Ser. No. 09/774,915, filed on Jan. 30, 2001, now U.S. Pat. No. RE 37,665, which is a reissue of U.S. Pat. No. 5,882,350 issued from U.S. patent application Ser. No. 09/002,535 filed on Jan 2, 1998, which is a continuation-in-part of U.S. patent application Ser. No. 08/843,972 filed on Apr. 17, 1997, now U.S. Pat. No. 5,888,204, which is a continuation-in-part of U.S. patent application Ser. No. 08/632,560 filed on Apr. 15, 1996, now U.S. Pat. No. 5,725,588, which is a continuation-in-part of U.S. patent application Ser. No. 08/421,087 filed on Apr. 13, 1995, now U.S. Pat. No. 5,520,690, U.S. patent application Ser. No. 09/002,535 filed on Jan. 2, 1998, now U.S. Pat. No. 5,882,530 is also a continuation of U.S. patent application Ser. No. 08/835,909 filed Apr. 10, 1997, now abandoned, which is a* continuation-in-part of prior application U.S. Ser. No. 08/663,383, entitled "A Polyaxial Pedicle Screw", filed Jun. 13, 1996, now U.S. Pat. No. 5,669,911 *which is a continuation-in-part of U.S. patent application Ser. No. 08/559,196 filed Nov. 13, 1995, now abandoned,* and which, in turn, was a continuation-in-part of Ser. No. 08/421,087, filed Apr. 13, 1995, now issued U.S. Pat. No. 5,520,690, entitled "An Anterior Spinal Polyaxial Locking Screw Plate Assembly".

BACKGROUND OF THE INVENTION

1. Field of the Invention

The invention relates generally to a polyaxial screw and coupling apparatus for use with orthopedic fixation systems. More particularly, the present invention relates to a screw for insertion into spinal bone, and a coupling element polyaxially mounted thereto, via a two-piece interlocking coupling element having a socket portion and a threaded compression member, for coupling the screw to an orthopedic implantation structure, such as a rod, therein enhancing the efficacy of the implant assembly by providing freedom of angulation among the rod, screw and coupling element.

2. Description of the Prior Art

The bones and connective tissue of an adult human spinal column consists of more than the 20 discrete bones coupled sequentially to one another by a tri-joint complex which consist of an anterior disc and the two posterior facet joints, the anterior discs of adjacent bones being cushioned by cartilage spacers referred to as intervertebral discs. These more than 20 bones are anatomically categorized as being members of one of four classifications: cervical, thoracic, lumbar, or sacral. The cervical portion of the spine, which comprises the top of the spine, up to the base of the skull, includes the first 7 vertebrae. The intermediate 12 bones are the thoracic vertebrae, and connect to the lower spine comprising the 5 lumbar vertebrae. The base of the spine is the sacral bones (including the coccyx). The component bones of the cervical spine are generally smaller than those of the thoracic and lumbar spine. For the purpose of this disclosure, however, the word spine shall refer only to the cervical region.

Referring now to FIGS. 1, 2 and 3, top, side, and posterior views of a vertical body, a pair of adjacent vertebral bodies, and a sequence of vertebral bodies are shown, respectively. The spinal cord is housed in the central canal 10, protected from the posterior side by a shell of bone called the lamina 12. The lamina 12 includes a rearwardly and downwardly extending portion called the spinous process 16, and laterally extending structures which are referred to as the transverse processes 14. The anterior portion of the spine comprises a set of generally cylindrically shaped bones which are stacked one on top of the other. These portions of the vertebrae are referred to as the vertebral bodies 20, and are each separated from the other by the intervertebral discs 22. The pedicles 24 comprise bone bridges which couple the anterior vertebral body 20 to the corresponding lamina 12.

The spinal column of bones is highly complex in that is includes over twenty bones coupled to one another, housing and protecting critical elements of the nervous system having innumerable peripheral nerves and circulatory bodies in close proximity. In spite of these complexities, the spine is a highly flexible structure, capable of a high degree of curvature and twist is nearly every direction. Genetic or developmental irregularities, trauma, chronic stress, tumors, and disease, however, can result in spinal pathologies which either limit this range of motion, or which threaten the critical elements of the nervous system housed within the spinal column. A variety of systems have been disclosed in the art which achieve this immobilization by implanting artificial assemblies in or on the spinal column. These assemblies may be classified as anterior, posterior, or lateral implants. As the classifications suggest, lateral and anterior assemblies are coupled to the anterior portion of the spine, which is the sequence of vertebral bodies. Posterior implants generally comprise pairs of rods, which are aligned along the axis which the bones are to be disposed, and which are then attached to the spinal column by either hooks which couple to the lamina or attach to the transverse processes, or by screws which are inserted through the pedicles.

"Rod assemblies " generally comprise a plurality of such screws which are implanted through the posterior lateral surfaces of the laminae, through the pedicles, and into their respective vertebral bodies. The screws are provided with upper portions which comprise coupling elements, for receiving and securing an elongate rod therethrough. The rod extends along the axis of the spine, coupling to the plurality of screws via their coupling elements. The rigidity of the rod may be utilized to align the spine in conformance with a more desired shape.

It has been identified, however, that a considerable difficulty is associated with inserting screws long a misaligned curvature and simultaneously exactly positioning the coupling elements such that the rod receiving portions thereof are aligned so that the rod can be passed therethrough without distorting the screws. Attempts at achieving proper alignment with fixed screws is understood to require increased operating time, which is known to enhance many complications associated with surgery. Often surgical efforts with such fixed axes devices cannot be achieved, thereby rendering such instrumentation attempts entirely unsuccessful.

The art contains a variety of attempts at providing instrumentation which permit a limited freedom with respect to angulation of the screw and the coupling element. These teachings, however, are generally complex, inadequately reliable, and lack long-term durability. These considerable drawbacks associated with prior art systems also include difficulty properly positioned the rod and coupling elements, and the tedious manipulation of the many small parts in the operative environment.

It is, therefore, the principal object of the present invention to provide a pedicle screw and coupling element assembly which provides a polyaxial freedom of implantation angulation with respect to rod reception.

In addition, it is an object of the present invention to provide such an assembly which comprises a reduced number of elements, and which correspondingly provides for expeditious implantation.

Accordingly it is also an object of the present invention to provide an assembly which is reliable, durable, and provides long term fixation support.

Other objects of the present invention not explicitly stated will be set forth and will be more clearly understood in conjunction with the description of the preferred embodiments disclosed hereafter.

SUMMARY OF THE INVENTION

The preceding objects of the invention are achieved by the present invention which is a polyaxial locking screw and coupling element for use with rod stabilization and immobilization systems in the spine. More particularly, the polyaxial screw and coupling element assembly of the present invention comprises a bone screw having a head which is curvate in shape, for example semi-spherical, and a two-piece interlocking coupling element mounted thereto. This combination is mounted inside the bottom of an internal channel of a cylindrical body member.

More specifically, with respect to the cylindrical body member, the tubular body comprises a rod receiving channel formed in the upper portion thereof, with a threading formed on the remaining upper elements so that a rod securing nut and/or set screw may be threaded thereon once a rod has been placed in the channel. The body further includes an axial bore which includes extends from the rod receiving channel through to the bottom of the cylinder. The portion of the axial bore which is below the channel forms a receiving chamber, the upper portion thereof having a constant diameter, and the lower portion of the chamber being inwardly tapered. The inner surface of the upper portion of the chamber and/or the inner surface of the portion of the axial bore which is above the chamber may further include a threading.

The two-piece interlocking coupling element comprises and socket portion and a cap portion. The socket portion is designed with an interior semi-spherical volume, so that it may receive the semi-spherical head of a corresponding bone screw. The interior volume of the socket portion is open at both axial ends thereof. The exterior surface of the socket portion, at the bottom thereof, includes a first set of slots which extend upwardly from the opening so that the interior semi-spherical volume may be expanded or contracted by the application of a radial force. In addition, the exterior surface at the bottom is tapered so that it is narrower at the bottom than at a midpoint. This taper is designed to mate with and nest in the tapered lower portion of the socket portion of the axial bore of the body member.

The upper exterior surface of the socket portion comprises a second set of slots, directed axially along the element to the midpoint, such that the upper opening of the socket element may expand and contract in accordance with the application of a radial force thereon. The exterior surface of this upper section of the socket portion is not tapered and is narrower than the widest taper portion of the bottom of the socket portion. The upper section, however, does further include an outwardly extending annular lip at the uppermost axial position. This upper section is designed to be inserted into, and joined with, the cap portion of the coupling element.

The cap portion has a generally cylindrical shape, having an open bottom. The open bottom is inwardly tapered, forming an inwardly extending annular lip, so that as the upper end of the socket portion is inserted, its upper slots are narrowed. Once axially inserted beyond this taper, the upper section of the socket portion expands outward over the inwardly extending annular lip. The inwardly extending annular lip engages the outwardly extending lip of the socket portion so as to prevent disengagement of the two pieces. The socket portion is then permitted to slide into the cap portion, until the larger diameter of the tapered lower portion of the socket contacts the entrance of the cap portion.

The exterior surface of the cap portion may be threaded, so that it may engage a threading of the upper portion of the socket portion and/or the inner surface of the axial bore which is above the socket portion. In addition, the top of the cap includes an opening so that a screw driving tool may directly engage the top of the screw.

The assembly of the entire device begins with the joining of the socket portion to the cap portion of the two-piece interlocking coupling element. This is achieved by the slideable interlocking mating of the two elements. Next, the semi-spherical head of the screw is inserted into the socket portion through the lower expandable opening in the taper portion. Once these parts have been assembled the screw and coupling element should be polyaxially rotatable relative to one another. The screw and coupling element are then inserted through the axial boe of the body (which may require the threading the cap portion of the coupling element along the threading on the inner surface of the axial bore and/or the threading of the cap along the threading of the upper portion of the chamber) until the socket portion nests in the tapered lower portion of the axial bore. If the upper portion of the chamber includes a threading it should not extend beyond the point of the initial nesting of the coupling element in the chamber. This is important because the cap portion must be able to move relative to the socket portion.

In this initial position, the top of the cap portion should rest above the bottom of the rod receiving channel so that a rod, when placed therein, seats directly onto the top of the cap. This direct contact provides the downward force necessary to compress the coupling element into the chamber so that the socket portion is compressed in the tapered portion and locks to the head of the screw.

In a preferred variation of this embodiment, the interior surface of the cap portion includes a slight narrowing taper so that as the cap is compressed downward by the rod, the upper slots of the socket portion are also narrowed, further increasing the crush locking effect on the head of the screw.

The implantation of this screw by a surgeon may proceed first by the assembly of the screw into its initial state. The shaft of the screw is then driven into the vertebral bone at the desired angulation. A rod is then introduced into the rod receiving channel, and the body is angulated into the most ideal position for receiving the rod. A nut and/or set screw is then used to secure the rod in the channel, and simultaneously to provide a sufficient downward translational force to cause the socket portion to be driven into the tapered portion of the chamber in the axial bore, and further to cause the cap portion to drive downwardly also (this further compression locking the screw head in the embodiment wherein the sliding of the cap portion toward the socket portion provides an additional compression on the top of the socket portion and therefore onto the head of the screw).

In a preferred variation, the locking nut comprises a cap nut which has a central post which is designed to provide additional structural support to the inner walls of the element at the top thereof, as well as providing a central seating pressure point for locking the rod in the channel. In either variation, the locking nut seats against the rod and prevents it from moving translationally, axially and rotationally.

Multiple screw assemblies are generally necessary to complete the full array of anchoring sites for the rod immobilization system, however, the screw assembly of the present invention is designed to be compatible with alternative rod systems so that, where necessary, the present invention may be employed to rectify the failures of other systems when the surgery may have already begun.

DETAILED DESCRIPTION OF THE PEFERRED EMBODIMENT

While the present invention will be described more fully hereinafter with reference to the accompanying drawings, in which particular embodiments and methods of implantation are shown, it is to be understood at the outset that persons skilled in the art may modify the invention herein described while achieving the functions and results of this invention. Accordingly, the descriptions which follow are to be understood as illustrative and exemplary of specific structures, aspects and features within the broad scope of the present invention and not as limiting of such broad scope.

Figure 2:
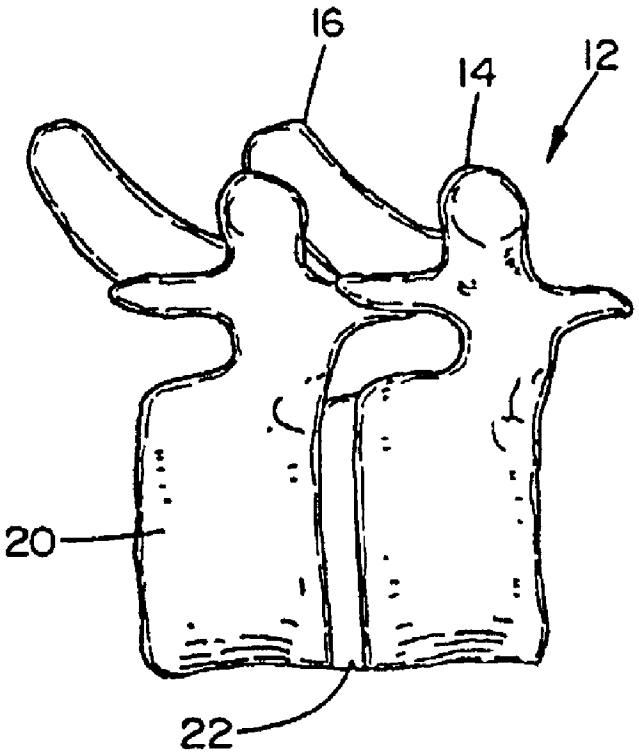
FIG. 2 is a side view of a pair of adjacent vertebrae of the type shown in FIG. 1.
Figure 1:
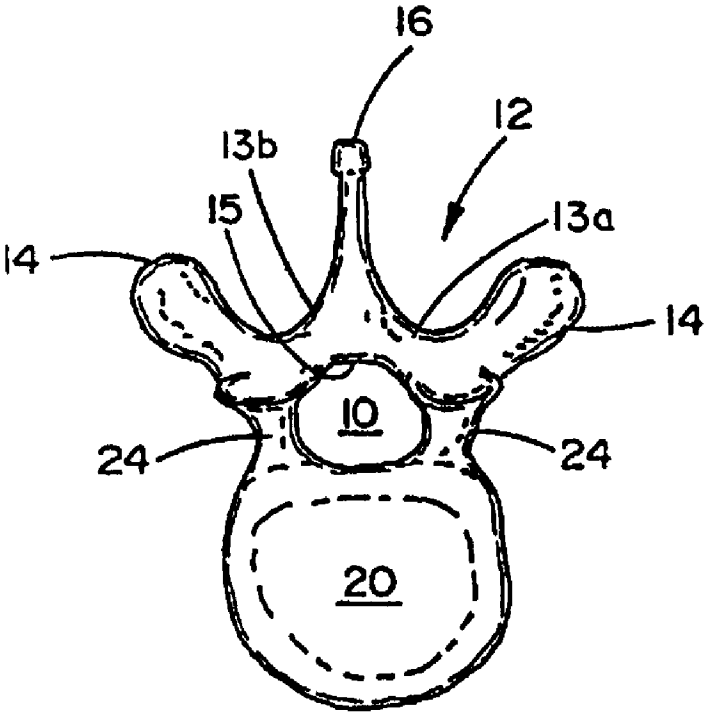
FIG. 1 is a top view of a human vertebra, which is representative of the type for which the present invention is useful for coupling thereto a rod apparatus.
Figure 3:
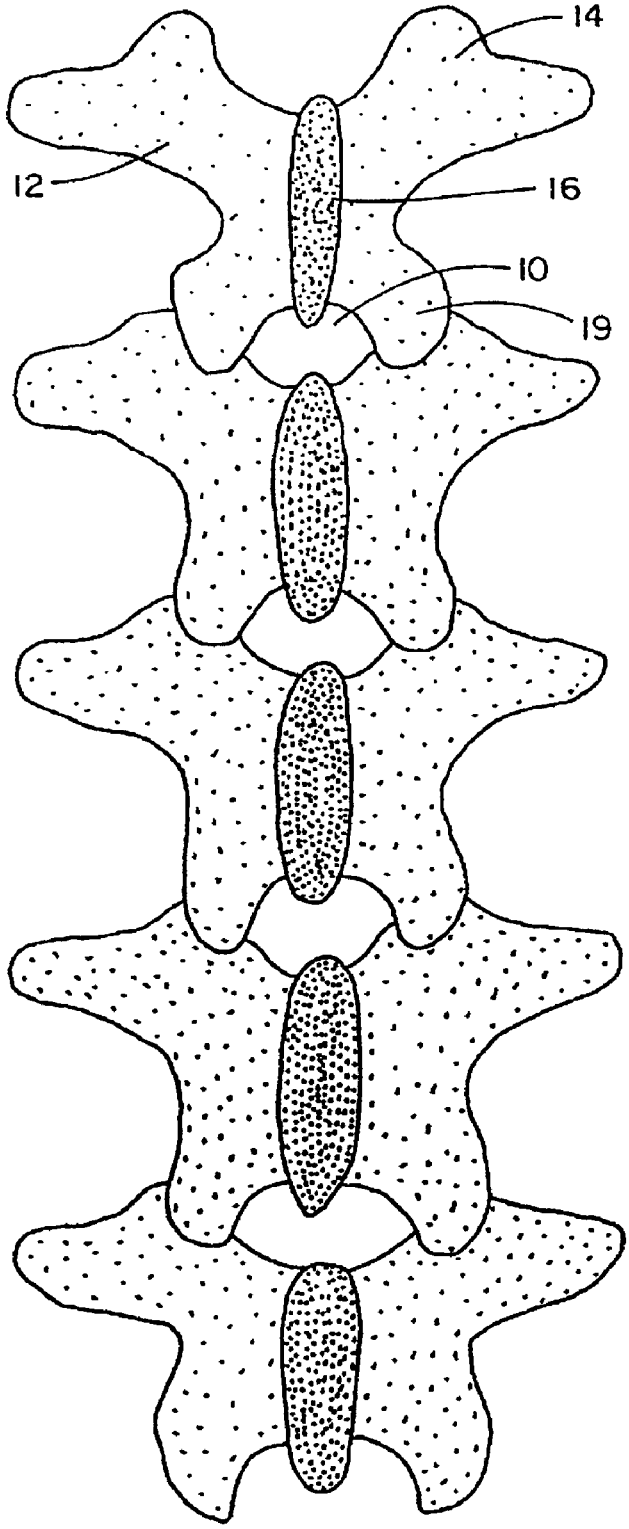
FIG. 3 is a posterior view of a sequence of vertebrae of the type shown in FIGS. 1 and 2.
Figure 4:
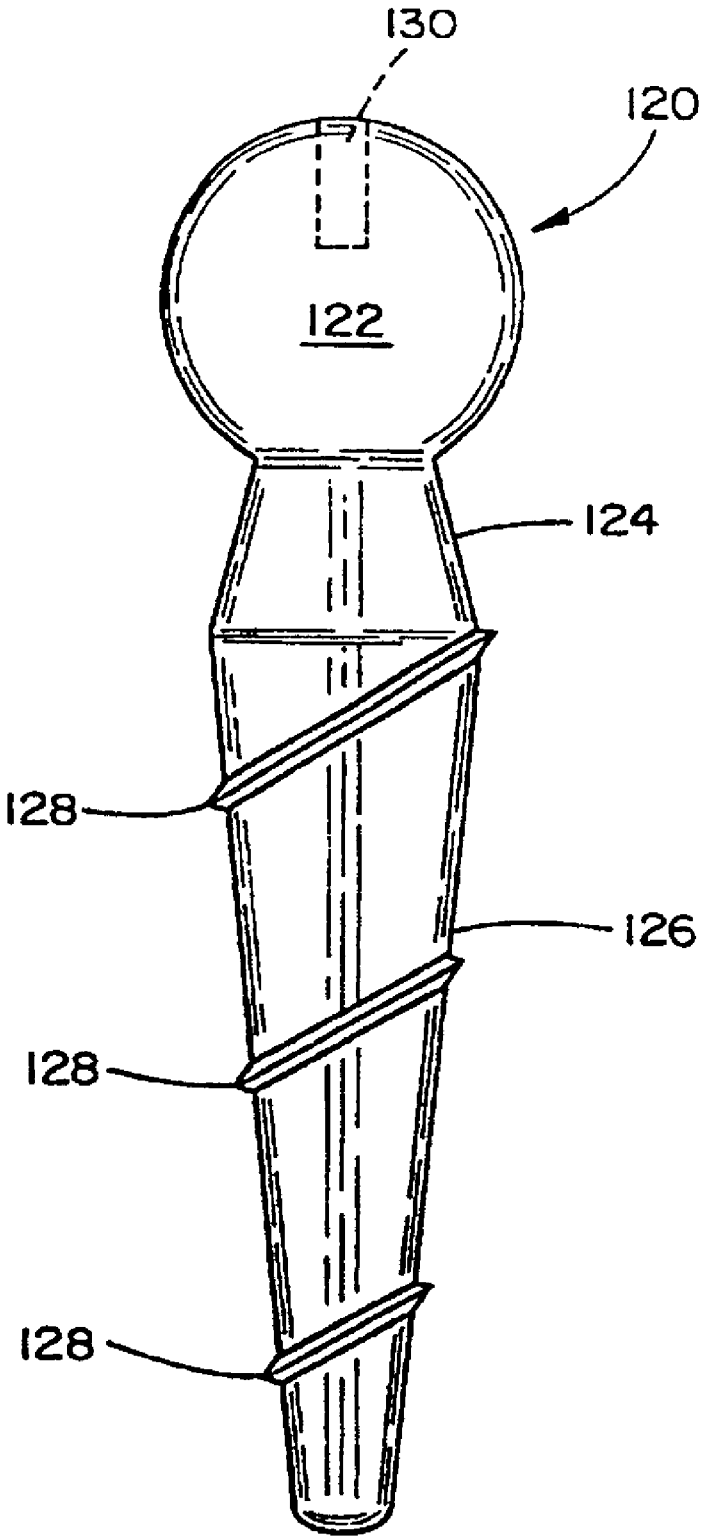
FIG. 4 is a side view of a screw having a curvate head which is an aspect of the present invention.

Referring now to FIG. 4, a side view of the screw portion of the present invention, comprising a curvate head, is shown. The screw 120 comprises a head portion 122, a neck 124, and a shaft 126. In FIG. 4, the shaft 126 is shown as having a tapered shape with a high pitch thread 128. It shall be understood that a variety of shaft designs are interchangeable with the present design. The specific choice of shaft features, such as thread pitch, shaft diameter to thread diameter ratio, and overall shaft shape, should be made be the physician with respect to the conditions of the individual patient's bone, however, this invention is compatible with a wide variety of shaft designs.

The head portion 122 of the screw 120 comprises a semi-spherical shape, which has a recess 130 in it. It is understood that the semi-spherical shape is a section of a sphere, in the embodiment shown the section is greater in extent than a hemisphere, and it correspondingly exhibits an external contour which is equidistant from a center point of the head. In a preferred embodiment, the major cross-section of the semi-spherical head 122 (as shown in the two dimensional illustration of FIG. 4) includes at least 270 degrees of a circle.

The recess 130 defines a receiving focus of the application of a torque for driving the screw 120 into the bone. The specific shape of the recess 122 may be chosen to cooperate with any suitable screw-driving tool. For example, the recess 130 may comprise a slot for a screwdriver, a hexagonally shaped hole for receiving an allen wrench, or most preferably, a threading for a correspondingly threaded post. It is further preferable that the recess 130 be co-axial with the general elongate axis of the screw 120, and most particularly with respect to the shaft 126. Having the axes of the recess 130 and the shaft 126 co-linear facilitates step of inserting the screw 120 into the bone.

The semi-spherical head portion 122 is connected to the shaft 126 at a neck portion 124. While it is preferable that the diameter of the shaft 126 be less than the diameter of the semi-spherical head 122, it is also preferable that the neck 124 of the screw 120 be narrower than the widest portion of the shaft 126. This preferable dimension permits the screw to swing through a variety of angles while still being securely joined to the locking collar (as set forth more fully with respect to FIGS. 5,8–9).

Figure 5:
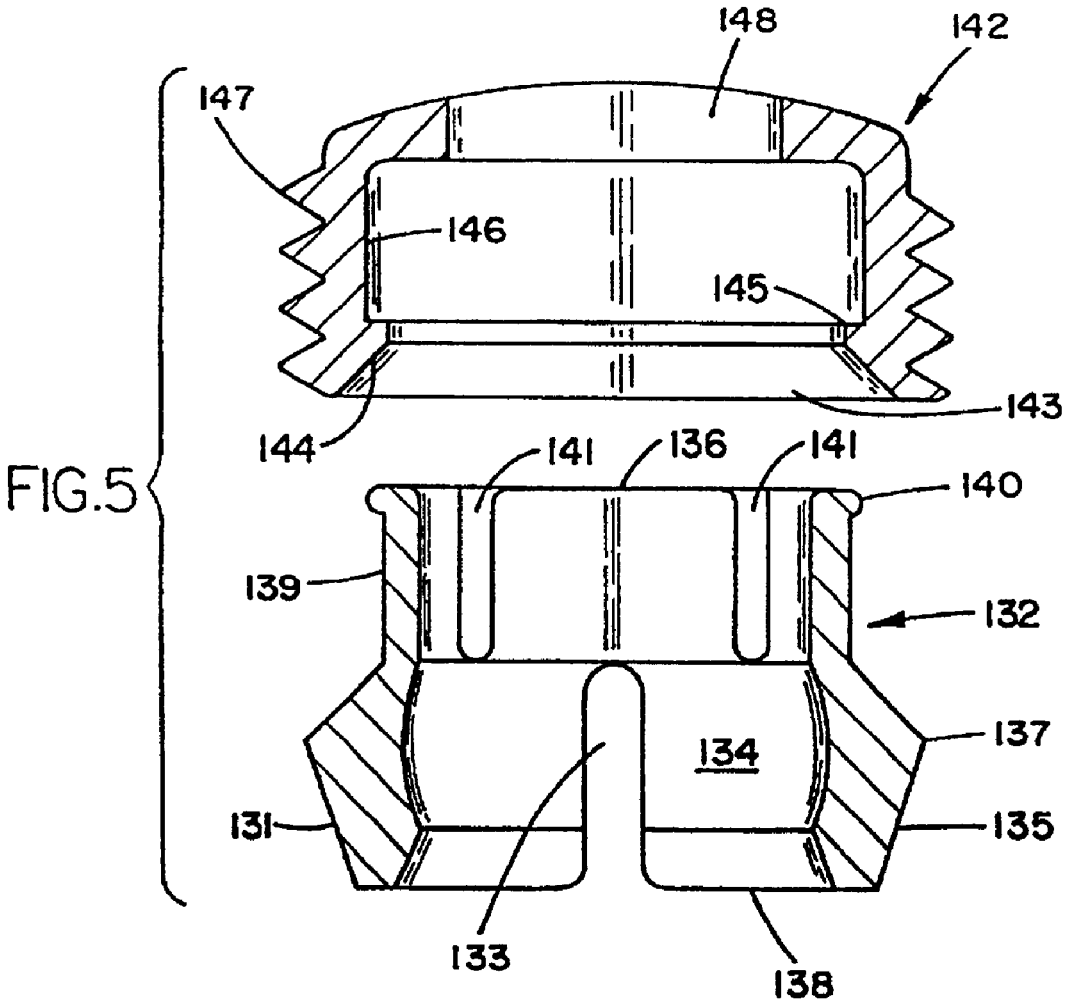
FIG. 5 is a side view of a two-piece interlocking coupling element of present invention.

Referring now to FIG. 5, the two elements which from the two-piece interlocking coupling element of the present invention are shown in a side cross-section view. Phantom lines show the interior structure of the elements long the diametrical cross section. With specific reference to the socket portion 132, the coupling element comprises a roughly cylindrical shape having an interior volume 134 in which the semi-pherical head 122 of the screw 120 is disposed. The interior volume 134 is open at the top 136 of the socket portion 132 and at the bottom thereof 138. The lower section 131 of the socket portion 132 comprises a set of slots 133 which extend vertically from the bottom 138 of the socket portion 132 to a position above the maximum diameter of the semi-spherical interior volume 134. These slots 133 permit the interior volume to expand and contract in accordance with the application of a radial force thereon. The external surface 135 of the lower section 131 of the socket portion 132 is tapered such that the narrowest part of the lower section 131 is at the bottom 138.

The upper section 139 of the socket portion 132 has a generally constant diameter, which is less than the diameter at the uppermost position 137 of the taper of the lower section 131. A second set of vertical slots 141 are provided in this upper section 139 so that it may also expand and contract in accordance with radial forces applied thereto. In addition, the uppermost end of this upper section 139 comprises an outwardly annular lip 140.

The cap portion 142 of the coupling element comprises an opening 143 in the bottom thereof, having an inwardly tapered entrance surface conformation 144. As the upper section 139 of the socket portion 132 is inserted into the opening 143 in the cap portion 142, the taper 144 of the opening 143 provides an inwardly directed force which causes the upper section 139 to contact (causes the slots 141 to narrow). This tapered entrance 144 opens to form an annular lip 145 which is useful for engaging and retaining the annular lip 140 of the upper section 139 of the socket portion 132. The interior surface 146 of the cap portion has a constant diameter, therein permitting the inserted upper section 139 of the socket portion 132 to slide and rotate relative to the cap portion 142.

Figure 7:
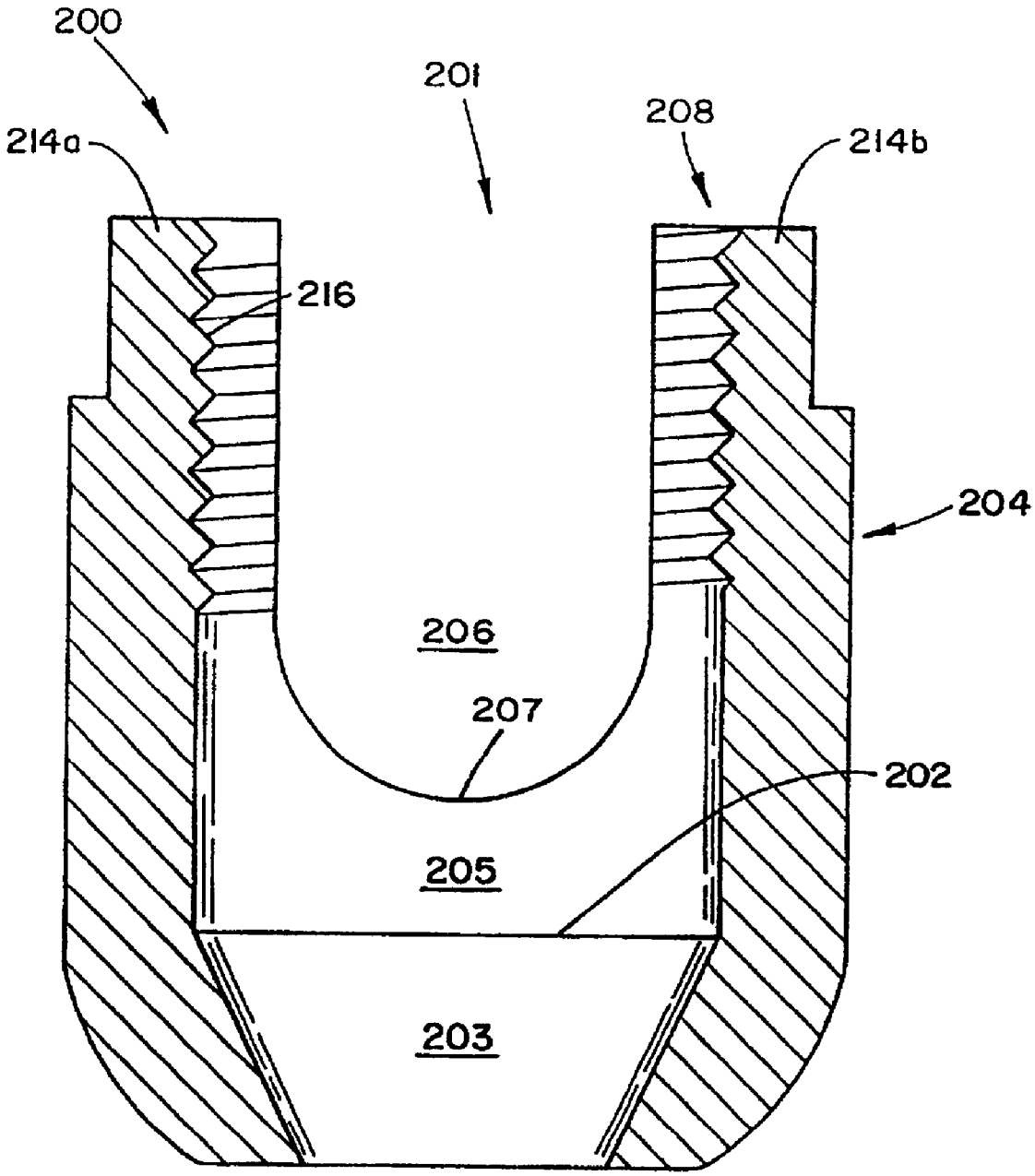
FIG. 7 is a side cross-sectional view of a cylindrical body having a chamber for receiving the two-piece interlocking coupling element and the screw of the present invention.

The exterior surface of the cap portion 142 comprises a threading 147 which is designed to engage threadings 211 disposed in the axial bore of the rod receiving body member (see FIG. 7). In addition, the cap portion 142 comprises an axial hole 148 through which a surgeon may insert a screw driving tool to access the head of the screw which is positioned in the interior volume 134 of the socket portion 132.

Figure 6:
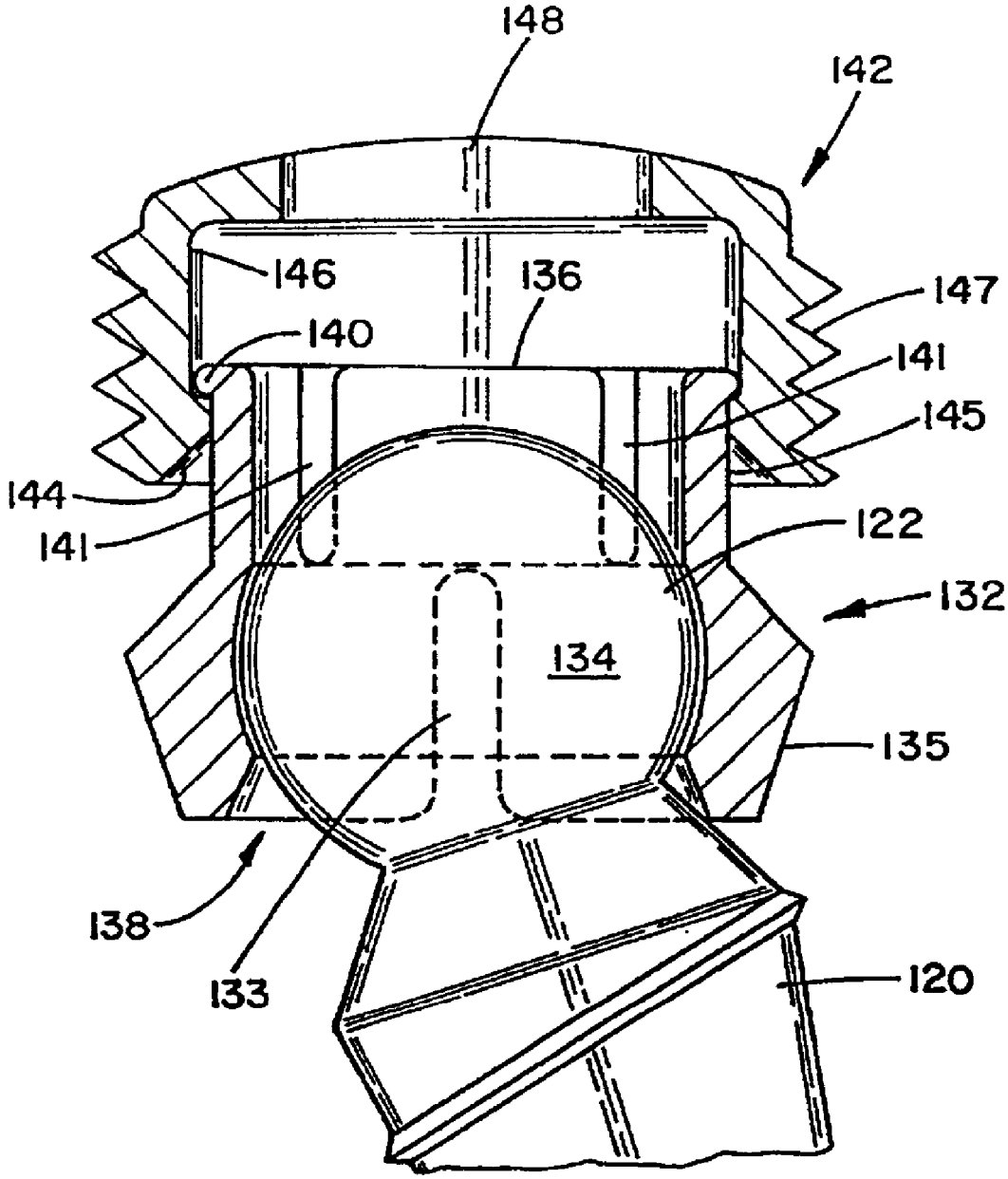
FIG. 6 is a side view of a two-piece interlocking coupling element of present invention mounted around the head of a screw of the type shown in FIG. 4.

More particularly, with respect to the disposition of the head 122 of the screw 120 in the socket portion 132, and with reference to FIG. 6, a partially assembled screw 120 and coupling element is shown in a side cross-section view.

The top 136 of the socket portion 132 is inserted into the opening in the cap portion 142 until the annular lip 140 of the socket 132 seats into the cap 142. The screw 120 is loosely held within the socket 132, which is, in turn, loosely retained within the cap 142.

Referring now to FIG. 7, the rod receiving body member 200 of the present invention is shown in a side view, wherein critical features of the interior of the element are shown in phantom. The body member 200, which comprises a generally cylindrical tubular body having an axial bore 201 extending therethrough, may be conceptually separated into a chamber portion 202 at the bottom of the axial bore 201, and an upper rod receiving channel portion 304, each of which shall be described more fully hereinbelow.

The upper rod receiving channel portion 204 of the body 200 includes a channel 206 formed therein, having rounded bottom surfaces 207. The channel 206, in turn, divides the walls of the cylindrical body of the upper portion 204 into a pair of upwardly extending members 214*a*, 214*b*. As shown in the embodiment illustrated in FIG. 7, the vertical distance from the top 208 of the channel to the curvate bottom 207 thereof, is larger than the diameter of the rod which is to be provided therein. This distance is necessarily larger than the diameter of the rod (see FIGS. 9 and 10) so that the rod may be fully nested in the channel 206. In addition, the depth of the curvate surface 207 of the channel is such that the cap portion 142 of the two-piece interlocking coupling element seats above the curvate bottom 207 of the body 200.

Figure 8:
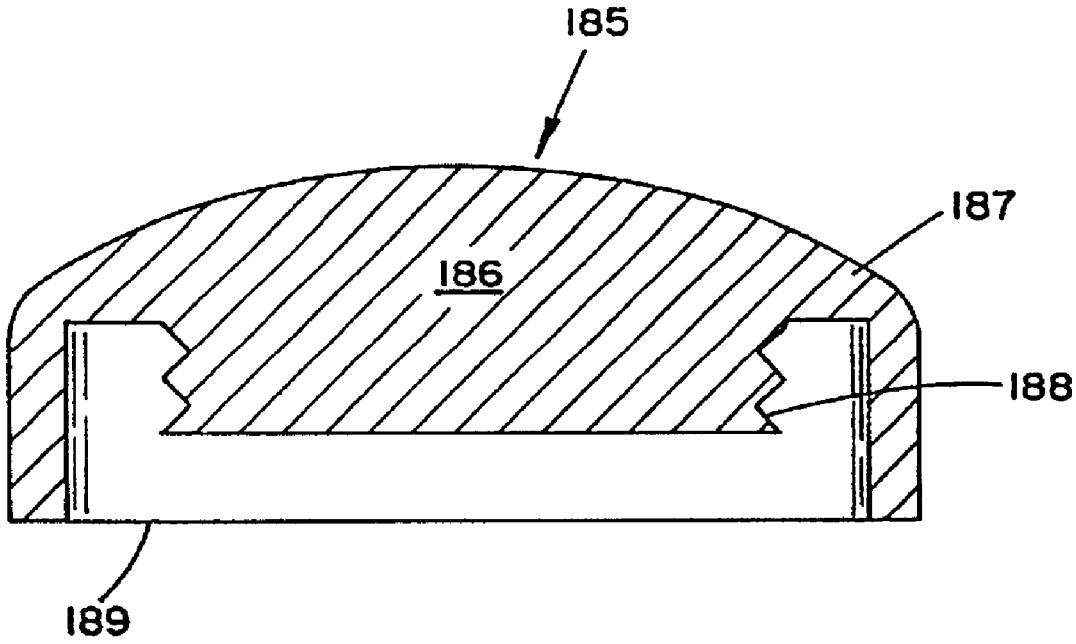
FIG. 8 is a side cross-sectional view of a top locking nut which is an aspect of the present invention.
Figure 9:
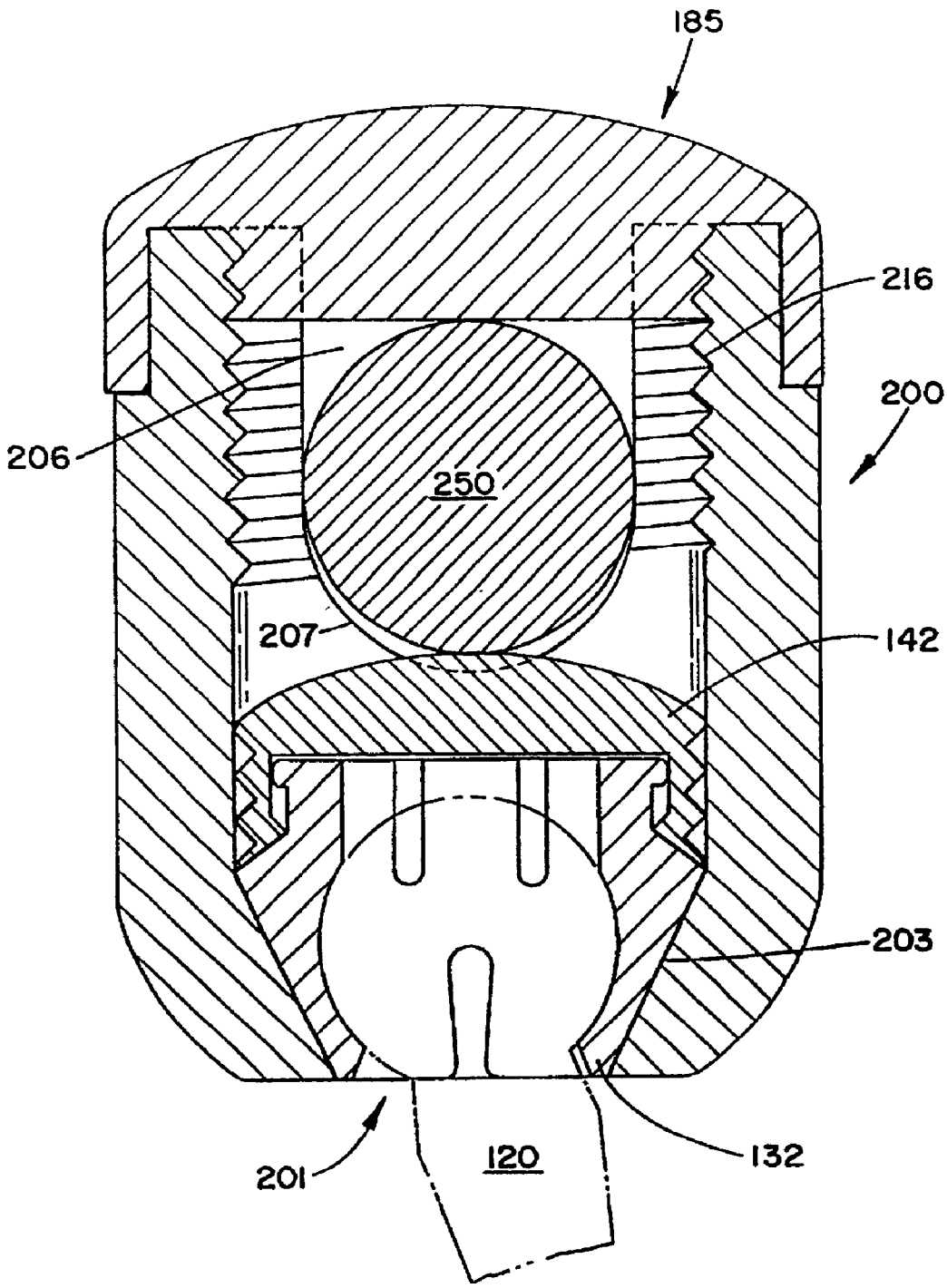
FIG. 9 is a side cross-sectional view of an embodiment of the present invention in its fully assembled disposition having a rod securely locked therein.
Figure 10:
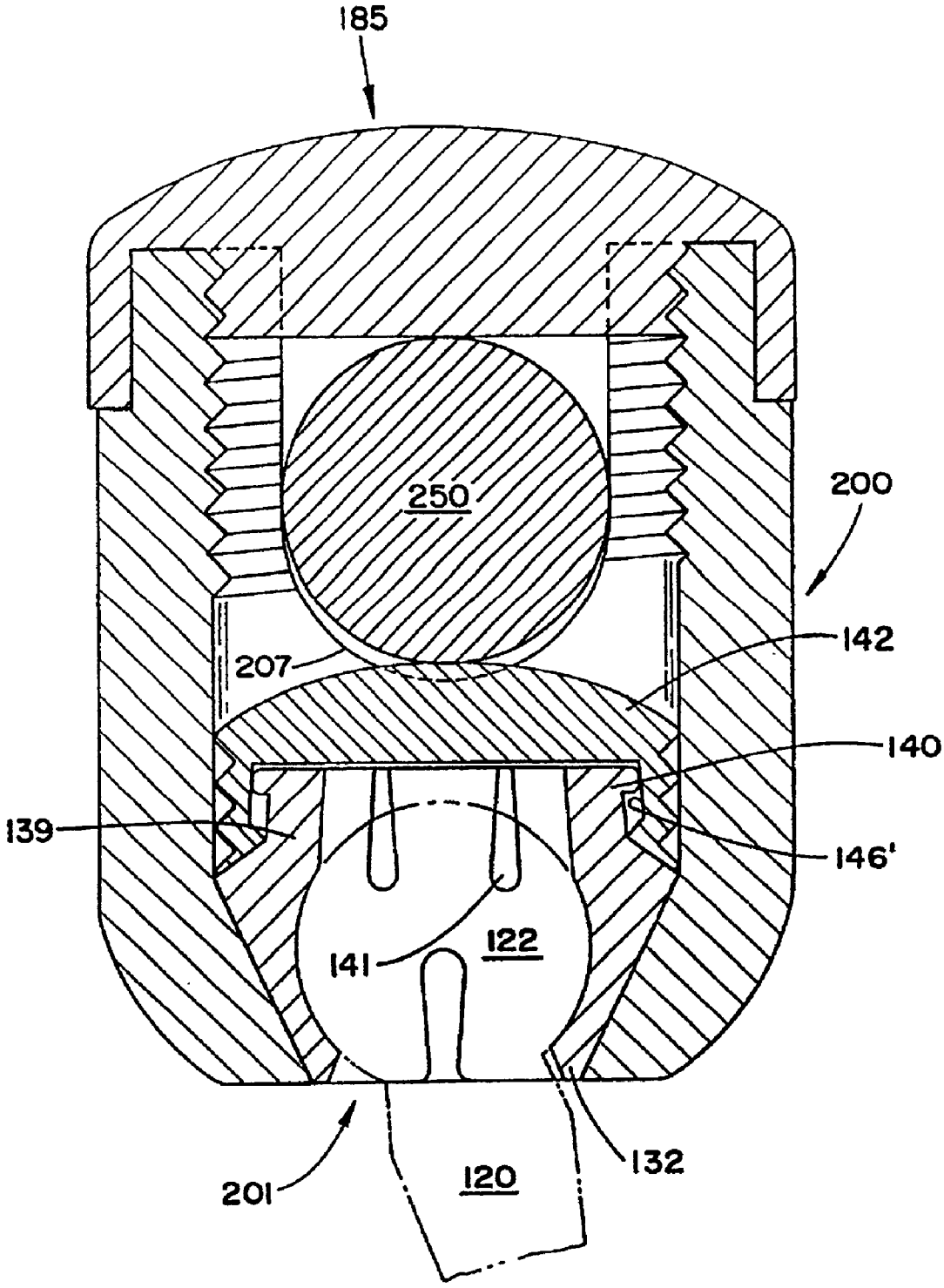
FIG. 10 is a side view of an alternative embodiment of the present invention in its fully assembled disposition having a rod securely locked therein.

The upwardly extending members 214*a*, 214*b* further have, disposed thereon, a threading 216 (which may be provided on the inner and/or outer circumferential surfaces, but which is shown in FIGS. 7, 9 and 10 as being on the inner circumferential surface). This threading 216 is ideally suited for receiving a top locking nut (see FIG. 8).

Referring now to the lower portion of the body, the chamber portion 202 can further be subdivided into a lower chamber portion 203 which includes an inwardly tapered surface, and an upper chamber portion 205 which has a constant diameter. The inwardly tapered portion 203 defines a nesting volume into which the socket portion 132 may nest. Prior to its being fully driven into this nesting volume, the socket portion 132 and the screw 120 disposed therein may be angulated relative to one another, and the screw 120 may be angulated relative to the body 200. Once driven fully into the tapered lower chamber portion 203, however, the taper of the axial bore 201 provides the necessary inwardly directed radial force to cause the socket portion 132 to crush lock to the head 122 of the screw 120.

The force which causes the socket portion 132 to be driven downwardly into the tapered lower chamber portion 203 is provided by the cap portion 142. More specifically, as stated above, when the initially assembled screw 120 and coupling element combination 132 and 142 (see FIG. 6) is advanced into the bottom of the axial bore 201 of the body 200, and the socket portion 132 nests in the lower chamber portion 203, the top of the cap portion 142 is positioned to receive the rod (see FIGS. 9 and 10) directly thereon. The locking of the rod in the channel 206 of the body 200 causes the cap portion 142 to be forced downwardly onto the socket portion 132, which in turn drives the socket portion 132 into the tapered lower chamber portion 203 and causes it of compression lock to the head 122 of the screw 120.

Referring now to FIG. 8, a top locking nut 185 is shown in side cross-section view. The nut 185 comprises post portion 186 and a flange portion 187, each of which is rotationally free, relative to the other. The post portion 186 includes a threading 188 thereon, for engaging and advancing along a threading 216 on the inner surface of the upwardly extending members 214*a*, 214*b* of the upper portion 204 of the body 200. The bottom surface 189 of the flange portion 187 (which does not rotate relative to the body as the post portion 186 is rotationally advanced) is intended to set against the top surface of the rod 250.

Referring now to FIG. 9, in which the fully assembled and body member 200, screw 120, coupling element portions 132 and 142, rod 250 and locking nut 185 are shown in side cross-section views, the implantation of this embodiment is described. First, the screw 120 and the two portions 132 and 142 of the coupling element are assembled into their initial association (see FIG. 6). The combination of the screw 120 and the two coupling element portions 132 and 142 are then advanced down the axial bore 201 of the body 200 until the socket portion 132 nests in the lower chamber 203 and the top of the cap portion 142 seats above the bottom 207 of the channel 206. (This insertion of the subassembly of the screw 120 and coupling element portions 132 and 142 into the axial bore 201 of the body 200 may require the threaded advance of the cap portion 142 long the interior threads 216 of the body).

The shaft of the screw 120 is then inserted and driven downward into the vertebral bone at the desired angle. Once properly positioned, the body 200 is rotated into the ideal rod receiving position. The rod 250 is then inserted into the channel 206 and the top locking nut 185 is threaded into the threading 216 and compresses the rod 250 to securely lock it in the channel 206. This downward force of the nut 185 and the rod 250 onto the cap portion 142 causes the cap portion to translate downward thus causing the socket portion 132 to translate downward in the tapered chamber 203 and contract to crush against the head 122 of the screw 120. The assembly is thereby fully locked in position.

Referring to FIG. 10, a variation of the above device is shown in a similar cross-section view. In this embodiment, the inner surface 146 of the cap portion 142 is tapered inwardly in the vertical direction so that the downward translation of the cap portion 142 causes the annular lip 140 of the socket portion 132 to be compressed inwardly. This causes the slots 141 of the upper section 139 of the socket portion 132 to narrow. This may be utilized to further clamp the interior volume 134 against the head 122 of the screw 120.

While there has been described and illustrated embodiments of a polyaxial screw and coupling element assembly for use with posterior spinal rod implantation apparatus, it will be apparent to those skilled in the art that variations and modifications are possible without deviating from the broad spirit and principle of the present invention. The present invention shall, therefore, be limited solely by the scope of the claims appended hereto.

We claim:

[1. A polyaxial screw and coupling element assembly for use with orthopedic rod implantation apparatus, comprising:

a screw having a semi-spherical head;

a cylindrical body including an axial bore defining a bottom chamber portion at a bottom end thereof and a rod receiving channel at a top end thereof, said bottom chamber portion further defining a tapered lower portion and a constant diameter upper chamber portion, and said top end having a threading thereon;

a two-piece interlocking coupling element including a socket portion having a semi-spherical interior volume for receiving therein the head of said screw, upper and lower sections, and vertical slots formed in said upper and lower sections, at least one of said slots rendering said interior volume expandable and contractable, said lower section having a tapered exterior surface for nesting in said tapered lower chamber portion of said cylindrical body such that forceable advancement of socket portion along the tapered lower chamber portion of the axial bore causes the at least one of said slots to narrow such that the semi-sperical interior volume contract, and a cap portion having an opening in a bottom thereof and an interior chamber extending upwardly therefrom for joining with, and slideably retaining therein, the upper section of said socket portion, said cap portion initially seating with a portion thereof extending into a bottom portion of said rod receiving channel; and a top locking nut, mateable with said threading, of locking a rod in said channel and for applying therethrough a downward force onto said cap portion, wherein said semi-spherical head portion is rotationally freely mounted within the semi-spherical interior volume of the socket portion prior to said socket portion being forceably advanced into the tapered lower chamber portion of the axial bore, and whereby downward compression of a rod in said channel portion of said body member, by said top locking nut, onto the cap portion causes the forceable advancement of the socket portion into the tapered lower chamber portion of the axial bore, and locks the screw, coupling element and body relative to one another.]

[2. The polyaxial screw as set forth in claim 1, wherein said semi-spherical head of said screw further includes a recess formed therein for receiving therein a screwdriving tool such that said screw may be threadably advanced into a vertebral bone.]

[3. The polyaxial screw as set forth in claim 1, wherein said threading on said top end is on the interior surface of said channel.]

[4. The polyaxial as set forth in claim 3, wherein said cap portion further includes a threading and wherein said cap portion needs to be threadably advanced along the threading to be seated in the bore into its initial position.]

[5. The assembly as set forth in claim 1, wherein said socket portion further comprises a substantially constant diameter upper section having an outwardly annular extending lip at an extreme end thereof, wherein said opening in the bottom of the cap portion comprises an inwardly directed annular lip, and wherein at least one of said vertical slots in the upper section thereof to be expandable and contractable such that the upper section of the socket portion may be forceably inserted into the opening in the bottom of the cap portion so that is may be retained in the interior chamber therein by mutual interference engagement of the inwardly directed annular lip of the cap portion and the outwardly extending annular lip of the socket portion.]

[6. The assembly as set forth in claim 5, wherein the interior chamber of the cap portion comprises a tapered surface such that advancement thereof into the hole causes an inwardly directed force against the upper section of the socket portion, therein causing the at least one of said vertical slots in the upper section to narrow and causes the upper section to contract and further lock the head of the screw within the interior semi-spherical volume of the socket portion.]

[7. An orthopedic implant apparatus having a rod and a plurality of screw and coupling element assemblies, comprising:

at least one screw having a semi-spherical head;

at least one cylindrical body including an axial bore defining a bottom chamber portion at a bottom end thereof and a rod receiving channel at a top end thereof, said bottom chamber portion further defining a tapered lower portion and a constant diameter upper chamber portion, and said top end having a threading thereon;

at least one corresponding two-piece interlocking coupling element including a socket portion having a semi-spherical interior volume for receiving therein the head of said corresponding screw, upper and lower sections, and vertical slots formed in said upper and lower sections, at least one of said slots rendering said interior volume expandable and contractable, said lower section having a tapered exterior surface for nesting in said corresponding tapered lower chamber portion of said cylindrical body such that forceable advancement of socket portion along the tapered lower chamber portion of the axial bore causes the at least one of said slots to narrow such that the semi-spherical interior volume contract, and a cap portion having an opening in a bottom thereof and an interior portion having an opening in a bottom thereof and an interior chamber extending upwardly therefrom for joining with, and slideably retaining therein, the upper section of said socket portion, said cap portion initially seating with a portion thereof extending into a bottom portion of said rod receiving channel; and at least one corresponding top locking nut, mateable with said threading, for locking a rod in said channel and for applying therethrough a downward force onto said cap portion, wherein said semi-spherical head portion is rotationally freely mounted within the semi-spherical interior volume of the socket portion prior to said socket portion being forceably advanced into the tapered lower chamber portion of the axial bore, and whereby downward compression of a rod in said channel portion of said body member, by said top locking nut, onto the cap portion causes the forceable advancement of the socket portion into the tapered lower chamber portion of the axial bore, and locks the screw, coupling element and body relative to one another.]

[8. The apparatus as set forth in claim 7, wherein said threading on said top end is on the interior surface of said channel.]

[9. The apparatus as set forth in claim 8, wherein said cap portion further includes a threading and wherein said cap portion needs to be threadably advanced along the threading to be seated in the bore into its initial position.]

[10. The apparatus as set forth in claim 7, wherein said socket portion further comprises a substantially constant diameter upper section having an outwardly annular extending lip at an extreme end thereof, wherein said opening in the bottom of the cap portion comprises an inwardly directly annular lip, and wherein at least one of said vertical slots in the upper section of said socket portion renders the upper section thereof to be expandable and contractable such that the upper section of the socket portion may be forceably inserted into the opening in the bottom of the cap portion so that it may be retained in the interior chamber therein by mutual interference engagement of the inwardly directed annular lip of the cap portion and the outwardly extending annular lip of the socket portion.]

[11. The apparatus as set forth in claim 10, wherein the interior chamber of the cap portion comprises a tapered surface such that advancement thereof into the hole causes an inwardly directed force against the upper section of the socket portion, therein causing the at least one of said vertical slots in the upper section to narrow and causes the upper section to contract and further lock the head of the screw within the interior semi-spherical volume of the socket portion.]

*12. An orthopedic device for securing immobilizing structures to sequences of bone, comprising:*

*a screw having a semi-spherical head and a threaded shaft;*

*a coupling element having an axial hole extending therethrough, a portion of the axial hole defining an interior volume for receiving therein the semi-spherical head of the screw that the threaded shaft may be moved through a variety of angles relative to the axial hole, the coupling element further including at least one slot rendering at least the interior volume deformable, the coupling element further including a tapered exterior surface, the coupling element further comprising a two-part interlocking coupling element including:*

*a socket portion containing the interior volume, the interior volume being semi-spherical shaped, the socket portion further including upper and lower sections, and at least one vertical slot formed in each of the upper and lower sections, at least one of the slots rendering the interior volume deformable, the lower section having the tapered exterior surface; and*

*a cap portion having an opening in a bottom thereof and an interior chamber extending upwardly therefrom for joining with, and slideably retaining therein, the upper section of the socket portion;*

*a receiving member including a through hole having an interior wall surface, a portion of the interior wall surface of the through hole being shaped to receive the coupling element and the screw when the semi-spherical head of the screw is mounted within the coupling element; and*

*wherein advancement of the screw through the through hole relative to the receiving member when the exterior surface of the coupling element engages the interior wall surface of the through hole prevents the coupling element from further advancement through the hole, preventing the semi-spherical head of the screw from advancing further through the through hole, and causing locking of the screw relative to both the coupling element and to the receiving member thereby locking the angle of the screw relative to the axial hole.*

*13. The assembly as set forth in claim 12 wherein the semi-spherical head of the screw further includes a recess formed therein for receiving therein a screwdriving tool such that the screw may be advanced into a vertebral bone.*

*14. The assembly as set forth in claim 12, wherein the cap portion further includes a threading.*

*15. An orthopedic implant apparatus comprising:*

*a fixation element having a semi-spherical head and a shaft extending therefrom;*

*a receiving member including an axial bore defined by an interior surface wall, a portion of the axial bore having a tapered portion;*

*a socket portion having a semi-spherical interior volume for receiving therein the semi-spherical head, and an exterior surface capable of nesting against the interior surface wall of the tapered portion, the socket portion being located in the axial bore of the receiving member, the socket portion further including:*

*upper and lower socket sections, and at least one vertical slot formed in at least one of the upper or lower sections, the at least one slot rendering the spherical interior volume deformable, where he exterior surface of the socket portion is tapered and located on the lower section; and*

*a cap portion having an opening in a bottom hereof and an interior chamber extending upwardly therefrom for joining with, and slideably retaining therein, the upper socket portion;*

*wherein the semi-spherical head is rotationally freely mounted within the semi-spherical interior volume of the socket portion prior to the socket portion being forcibly advanced against the interior surface wall of the tapered portion, and whereby after forcible advancement of the socket portion causes the fixation element, the socket portion and the receiving member to be locked relative to one another.*

*16. The assembly as set forth in claim 15 wherein the semi-spherical head of the fixation element further includes a recess formed therein for receiving therein a screwdriving tool such that the fixation element may be advanced into a vertebral bone.*

*17. The assembly as set forth in claim 15 wherein the cap portion further includes a threading.*

*18. An orthopedic implant apparatus comprising:*

*a fixation element having a semi-spherical head, having a lower and upper curvate surface, and a threaded shaft extending from the semi-spherical head;*

*a receiving member including an axial bore defined by an interior surface wall, the axial bore having a lower portion and an upper threaded portion;*

*a socket portion comtaining the semi-spherical head of the fixation element therein and having a lower socket portion and a threaded upper socket portion, the socket portion being moveably located in the axial bore;*

*wherein the lower socket portion has an interior volume defined by an interior surface which receives the lower curvate surface of the semi-spherical head, such that the threaded shaft is inserted through a hole in the*

*interior surface and is capable of being moved through a variety of angles relative to the socket portion, the lower socket portion further including an exterior surface which seats against the interior surface wall of the lower portion, the lower socket portion further including at least one vertical slot rendering the interior volume deformable; and*

*the threaded upper socket portion comprising a cap portion having an opening in a bottom thereof and an interior chamber extending upwardly therefrom for joining with, and slideably retaining therein, the lower socket portion, disposed above the upper curvate surface of the semi-spherical head of the fixation element, whereby downward pressure on the cap portion causes compression of the lower curvate surface against the interior surface of the lower socket portion to lock the fixation element relative to the socket portion, causing the upper and lower socket portions, the semi-spherical head of the fixation element, and the receiving member to be locked relative to one another.*

*19. The assembly as set forth in claim 18 wherein the semi-spherical head of the fixation element further includes a recess formed therein for receiving therein a screwdriving tool such that the fixation element my be threadably advanced into a vertebral bone.*

*20. The implant apparatus of claim 18 further comprising a locking nut engageable with the upper threaded portion of the receiving member, tightening of the locking nut with respect to the receiving member exerting a downward force onto a rod disposed in the receiving member such that the rod exerts a downward force on the cap portion.*

*21. A bone anchor and coupling member assembly wherein said coupling member is capable of being selectively positioned and locked at a plurality of angles relative to the bone anchor, said assembly comprising:*

*a bone anchor having a curvate head;*

*a coupling member having an axial bore for receiving said curvate head, said bore having an interior surface, and a channel formed herein for receiving an elongate member, at least a portion of said channel being in spatial communication with said bore;*

*a first intervening member positioned between the curvate head in the bore and an elongate member positioned in said channel; and*

*a second intervening member positioned in the bore between said curvate head and said interior surface,*

*wherein a force applied to said first intervening member urges said curvate head to translate axially within said bore and into locking contact with said second intervening member.*

*22. The assembly of claim 21 wherein said curvate head is semi-spherical.*

*23. The assembly of claim 21 wherein said bore includes at least two portions having different diameters.*

*24. The assembly of claim 23 wherein said second intervening member is positioned within one of said portions having different diameters.*

*25. The assembly as set forth in claim 21 wherein said second intervening member circumferentially retains the curvate head.*

*26. The assembly as set forth in claim 21 wherein the force applied to said first intervening member is provided through the elongate member positioned in the channel.*

*27. An orthopedic device comprising:*

*a screw having a semi-spherical head and a threaded shaft,*

*a coupling element having an axial hole extending therethrough for receiving therein the semi-spherical head of the screw that the screw may be moved through a variety of angles relative to the axial hole, the coupling element further including at least one slot; and*

*a receiving member including a through hole having an interior wall surface, a portion of the interior wall surface of the through hole being shaped to receive the coupling element and the screw when the semi-spherical head of the screw is mounted within the coupling element,*

*wherein engagement of the coupling element and the interior wall surface selectively prevents the screw from moving relative to the axial hole, thereby locking the angle of the screw relative to the axial hole.*

*28. The orthopedic device as set forth in claim 27 wherein the semi-spherical head of the screw further includes a recess formed therein for receiving therein a screwdriving tool such that the screw may be advanced into a vertebral bone.*

*29. The orthopedic device as set forth in claim 27 wherein the interior wall surface of the receiving member is tapered.*

*30. The orthopedic device as set forth in claim 27 wherein the interior wall surface of the receiving member and the exterior surface of the coupling element are tapered.*

*31. The orthopedic device as set forth in claim 27 wherein coupling element axial hole has a concave surface conforming to the semi-spherical screw head.*

* * * * *

UNITED STATES PATENT AND TRADEMARK OFFICE

CERTIFICATE OF CORRECTION

PATENT NO. : RE 39,089 E
APPLICATION NO. : 09/992612
DATED : May 2, 2006
INVENTOR(S) : James D. Ralph et al.

It is certified that error appears in the above-identified patent and that said Letters Patent is hereby corrected as shown below:

Column 9, line 37, delete “of” and add --for--;
Column 10, line 4, after the word “section” add --of said socket portion renders the upper section--;
Column 10, line 21, delete “orthopedic” and add --orthopaedic--;
Column 10, line 47, delete “an interior portion having an opening in a bottom”;
Column 10, line 48, delete “thereof and”;
Column 11, line 42, after the word “screw” add --such--;
Column 12, line 9, after “12” add --,--;
Column 12, line 30, delete “he” and add --the--;
Column 12, line 45, after “15” add --,--;
Column 12, line 50, after “15” add --,--;
Column 12, line 59, delete “comtaining” and add --containing--;
Column 13, line 21, after “18” add --,--;
Column 13, line 24, delete “my” and add --may--;
Column 14, line 3, after “21” add --,--;
Column 14, line 5, after “21” add --,--;
Column 14, line 7, after “23” add --,--;
Column 14, line 10, after “21” add --,--;
Column 14, line 13, after “21” add --,--;
Column 14, line 21, after “screw” (first instance) add --such--;
Column 14, line 34, after “27” add --,--.

Signed and Sealed this

Twenty-eighth Day of August, 2007

JON W. DUDAS
*Director of the United States Patent and Trademark Office*